(12) United States Patent
Jacob et al.

(10) Patent No.: US 6,689,165 B2
(45) Date of Patent: Feb. 10, 2004

(54) SURFACE MODIFICATIONS FOR ENHANCED EPITHELIALIZATION

(75) Inventors: Jean T. Jacob, New Orleans, LA (US); Jingjing Bi, River Ridge, LA (US)

(73) Assignee: Board of Supervisors of Louisana State University and Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 09/822,582

(22) Filed: Mar. 30, 2001

(65) Prior Publication Data

US 2002/0007217 A1 Jan. 17, 2002

Related U.S. Application Data

(60) Provisional application No. 60/193,528, filed on Mar. 31, 2000.

(51) Int. Cl.$^7$ .................................................. A61F 2/14
(52) U.S. Cl. ..................................... 623/5.16; 623/5.11
(58) Field of Search ......................... 623/4.1, 5.11–5.16

(56) References Cited

U.S. PATENT DOCUMENTS

| | | | |
|---|---|---|---|
| 4,865,601 A | 9/1989 | Caldwell et al. | 623/5 |
| 5,120,829 A | 6/1992 | Pierschbacher et al. | 530/326 |
| 5,123,921 A | 6/1992 | Werblin et al. | 623/5 |
| 5,171,264 A | 12/1992 | Merrill | 623/3 |
| 5,278,063 A | 1/1994 | Hubbell et al. | 435/240.243 |
| 5,376,375 A | * 12/1994 | Rhee et al. | 424/423 |
| 5,512,474 A | 4/1996 | Clapper et al. | 435/240.243 |
| 5,654,267 A | 8/1997 | Vuori et al. | 514/2 |
| 5,677,276 A | 10/1997 | Dickerson et al. | 514/8 |
| 5,716,633 A | 2/1998 | Civerchia | 424/428 |
| 5,760,176 A | 6/1998 | Pierschbacher et al. | 530/326 |
| 5,830,504 A | 11/1998 | Vuori et al. | 424/484 |
| 5,836,313 A | 11/1998 | Perez et al. | 128/898 |
| 5,906,828 A | 5/1999 | Cima et al. | 424/423 |
| 5,986,043 A | 11/1999 | Hubbell et al. | 528/354 |
| 6,045,818 A | 4/2000 | Cima et al. | 424/423 |

OTHER PUBLICATIONS

Altankov, G. et al., "Reorganization of substratum–bound fibronectin on hydrophilic and hydrophobic materials is related to biocompatibility," J. Mater. Sci. Mater. Med., vol. 5, pp. 732–737 (1994).
Anderson, J.M., "Inflammatory response to implants," Trans. Am. Soc. Artif. Intern. Organs., vol. 34, pp. 101–107 (1988).
Andrade, J.D. et al., "Protein adsorption and materials biocompatibility: A tutorial review and suggested hypothesis," Prog. Surface Sci., vol. 79, pp. 1–63 (1986).
Aota, S. et al., "The short amino acid sequence Pro–His–Ser– Arg–Asn in human fibronectin enhances cell–adhesive function," J. Biol. Chem., vol. 269, pp. 24756–24761 (1994).
Beekhuis, W.H. et al., "Complications of hydrogel intracorneal lenses in monkeys," Arch. Ophthalmol., vol. 105, pp. 116–122 (1987).
Berman, M., "The pathogenesis of corneal epithelial defects," In *Healing Processes in the Cornea*, (Beuerman et al. eds), Portfolio Publishing Company, The Woodlands, Texas, pp. 15–26 (1989).
Bohnert, J.L. et al., "Adsorption of proteins from artifical tear solutions to contact lens materials," Invest. Ophthalmol. Vis. Sci., vol. 29, pp. 362–373 (1988).
Bruck, S.D., "Physiocochemical aspects of the blood compatibility of polymer surfaces," J. Polymer Sci., Polymer Symp., vol. 66, pp. 283–312 (1979).
Castillo, E.J. et al., "Characterization of protein adsorption on soft contact lenses. I. Conformational changes of adsorbed human serum albumin," Biomaterials, vol. 5, pp. 319–325 (1984).
Castillo, E.J. et al., "Protein adsorption on hydrogels. II. Reversible and irreversible interactions between lysozyme and soft contact lens surfaces," Biomaterials, vol. 6, pp. 338–345 (1985).
Crawford, C.J. et al., "Tissue interaction with hydrogel sponges implanted in the rabbit cornea," Cornea, vol. 12(4), pp. 348–357 (1993).
Crawford, G.J. et al., "Preliminary evaluation of a hydrogel core–and–skirt keratoprosthesis in the rabbit cornea," J. Refract. Surg., vol. 12, pp. 525–529 (1996).
Crosson, C.E. et al., "Epithelial wound closure in the rabbit cornea: A biphasic process," Invest. Ophthalmol. Vis. Sci., vol. 21, pp. 464–473 (1986).

(List continued on next page.)

*Primary Examiner*—Corrine McDermott
*Assistant Examiner*—William H. Matthews
(74) *Attorney, Agent, or Firm*—Bonnie J. Davis; John H. Runnels

(57) ABSTRACT

A synthetic device for cornea augmentation and replacement that increases corneal epithelium cell adhesion and migration. Using tethered extracellular matrix proteins (ECMPs), corneal growth factors, and other ligand-specific corneal enhancer species (e.g., laminin, fibronectin, substance P, fibronectin adhesion-promoting peptide sequence, FAP, and insulin-like growth factor-1 [IGF-1]) on the polymeric surface of an artificial cornea, the epithelial cell response can be significantly enhanced. Other proteins of interest include, but are not limited to, k-laminin, talin, integrin, kalinin, fibroblast growth factor (FGF), and TGF-β. By tethering a combination of corneal enhancer molecules, a more natural environment can be created. Additionally, the surface topography of the artificial surface, preferably a hydrogel, can be micro-molded, etched, lathed, or engineered prior to tethering the corneal enhancer molecules to resemble the natural underlying surface of the corneal epithelial cells, Bowman's layer. This system allows epithelial cells to spread and attach faster than existing systems, as well as providing an underlying textured surface that allows the cells to resist the shear force induced in vivo by the blinking of the eyelid. Moreover, the resulting epithelial layer closely resembles a natural epithelial layer. The material can be used, for example, as a corneal onlay, an epikeratophakia lenticule, an intracorneal augmentation device, or an artificial cornea.

31 Claims, No Drawings

OTHER PUBLICATIONS

Dupont, D. et al., "Biocompatibility of human collagen type IV intracorneal implants," Cornea, vol. 8(4), pp. 251–258 (1989).

Friend, J. et al., "Biochemistry of the Cornea," in *The Cornea: Scientific Foundations and Clinical Pactice*, (Smolin et al. eds), Little, Brown and Co., U.S., pp. 47–67 (1994).

Fujiikawa, L.S. et al., "Fibronectin in healing rabbit cornea wounds," Lab. Invest., vol. 45, pp. 120 (1981).

Gipson, I.K. et al., "Anchoring fibrils form a complex network in human and rabbit cornea," Invest. Ophthalmol. Vis. Sci., vol. 28, pp. 212–220 (1987).

Glass, J.R. et al., "Characterization of a hyaluronic acid–Arg–Gly–Asp peptide cell attachment matrix," Biomaterials, vol. 17, pp. 1101–1108 (1996).

Goodman, S.L. et al., "Three–dimensional extracellular matrix textured biomaterials," Biomaterials, vol. 17, pp. 2087–2095 (1996).

Grant, M. et al., "effects of epidermal growth factor, nd transforming growth factor–$\beta$ on corneal cell chemotaxis," Invest. Ophthalmol. Vis. Sci., vol. 33, pp. 3292–3301 (1992).

Griffith Cima, L., "Polymer substrates for controlled biological interactions," J. Cell. Biochem., vol. 56, pp. 155–161 (1994).

Groth, T. et al., "Fibroblast spreading and proliferation on hydrophilic and hydrophobic surfaces is related to tyrosine phosphorylation in focal contacts," J. Biomater. Sci. Polymer Edn., vol. 7, pp. 297–305 (1995).

Groth, T. et al., "Studies on cell–biomaterial interaction: role of tyrosine phosphorylation during fibroblast spreading on surfaces varying in wettability," Biomaterials, vol. 17, pp. 1227–1234 (1996).

Groth, T.H. et al., "Adhesion of human peripheral lymphocytes on biomaterials preadsorbed with fibronectin and vitronectin," J. Biomater. Sci. Polymer Edn., vol. 6, pp. 729–739 (1994).

Grushkin–lerner, L.S. et al., "Expression of integrin receptors on plasma membranes of primary corneal epithelial cells is matrix specific," Exp. Eye Res. vol. 64, pp. 323–334 (1997).

Hanna, C. et al., "Cell production and migration in the epithelial layer of the cornea," Arch. Ophthalmol., vol. 64, pp. 536 (1960).

Hattori, S. et al., "Fibroblast cell proliferation on charged hydroxyethyl methacrylate copolymers," J. Colloid Interface Sci., vol. 104, pp. 72–78 (1985).

Helmus, M.N., "The effect of surface charge on arterial thrombosis," J. Biomed. Mater. Res., vol. 18, pp. 165–183 (1984).

Hern, D.L. et al., "Incorporation of adhesion peptides into nonadhesive hydrogels useful for tissue resurfacing," J. Biomed. Mater. Res., vol. 39, pp. 266–276 (1998).

Hiraki, S. et al., "Biochemical and histological findings on the effect of fibronectin in rabbits with experimental corneal disorders," Arzneim–Forch/Drug Res., vol. 40, pp. 1336–1340 (1990).

Hoffman, "S., "Blood–biomaterial interactions: an overview," In: Biomaterials: Interfacial Phenomena and Applications," (S.L. Cooper and N.A. Peppas (eds)), Advances in Chemistry Series 199, pp. 3–8(1982).

Horbett, T.A., "The role of adsorbed proteins in animal cell adhesion," Colloids and Surfaces B: Biointerfaces, vol. 2, pp. 225–240 (1994).

Horowitz, "et al., Interaction of plasma membrane fibronectin receptor with talin: a transmembrane linkage," Nature, vol. 320, pp. 531–533 (1986).

Jacob–LaBarre, J.T. et al., "Development of a soft artifical cornea for end stage corneal diseases," Proceedings of the American Chemical Society Division of Polymeric Materials: Science and Engineering, Los Angeles, vol. 59, pp 95–99 (1988).

Jacob–LaBarre, J.T. et al., "Development of a new type of artificial cornea for treatment of endstage corneal diseases," Progress in Biomedical Polymers, CG Gebelein and RL Dunn (eds.), Plenum Press, New York, pp. 27–39 (1990).

Jacob–LaBarre, J.T. et al., "Development of a practical artifical cornea for end stage corneal diseases," Transactions. Thirteenth Annual Meeting for the Society for Biomaterials, New York City, vol. X, p. 292 (1987).

Juliano, D.J. et al., "Effect of the conformation and orientation of adsorbed fibronectin on endothelial cell spreading and the strength of adhesion," J. Biomed. Mater. Res., vol. 27, pp. 1103–1113 (1993).

Kenyon, K.R. et al., "Regeneration of corneal epithelial basement membrane following thermal cauterization," Invest. Ophthalmol. Vis. Sci., vol. 16, pp. 292–301 (1977).

Khodadoust, A. et al., "Adhesion of regenerating corneal epithelium: the role of basement membrane," Am. J. Ophthalmol., vol. 65, pp. 339–348 (1968).

Kirkham, S.M. et al., "The keratoprosthesis: improved biocompatibility through design and surface modification," Ophthalmic Surg., vol. 22, pp. 455–461 (1991).

Klein, C.P. et al., "Activation of complement C3 by different calcium phosphate powders," Biomaterials, vol. 4, pp. 181–184 (1986).

Lampin, M. et al., "Correlation between substratum roughness and wettability, cell adhesion, and cell migration," J. Biomed. Mater. Res., vol. 36, pp. 99–108 (1997).

LeDuc, C.A. et al., "A mathematical model for the Vroman effect," Ind. Eng. Chem. Res., vol. 34, pp. 3488–3495 (1995).

Lin, H.–B. et al., "Synthesis, surface, and cell–adhesion properties of polyurethanes containg covalently grafted RGD–peptides," J. Biomed. Mater. Res., vol. 28, pp. 329–342 (1994).

Lyman, D.J. et al., "The effect of chemical structure and surface properties of polymers on the coagulation of blood. I. Surface free energy effects," Transact. Am. Soc. Artific. Intern. Organs., vol. XI, pp. 301–306 (1965).

Marinkovich, M.P. et al., "The dermal–epidermal junction of human skin contains a novel laminin variant," J.Cell Biol., vol. 119, pp. 696–703 (1992).

Massia, S.P. et al., "An RGD Spacing of 440 nm is sufficient for integrin $\alpha_v\beta_3$–mediated fibroblast spreading and 140 nm for focal contact and stress fiber formation," J. Cell. Biol., vol. 12, pp. 1089–1100 (1991).

Massia, S.P. et al., "Covalent surface immobilization of Arg–Gly–Asp– and Tyr–Ile–Gly–Ser–Arg–containing peptides to obtain well–defined cell–adhesive substrates," Analyt. Biochem., vol. 187, pp. 292–301 (1990).

Massia, S.P. et al., "Covalently immobilized laminin peptide Tyr–Ile–Gly–Ser–Arg (YIGSR) supports cell spreading and colocalization of the 67–kilodalton laminin receptor with α–actinin and vinculin," J. Biol. Chem., vol. 268, pp. 8053–8059 (1993).

Nishida, T. et al., "Expression of fibronectin receptors in corneal epithelial cells," In: Healing Processes in the Cornea (Beuerman RW, Crosson CE, Kaufman HE (eds)), Portfolio Publishing Company, The Woodlands, Texas, pp. 127–135 (1989).

Nishida, T. et al., "Fibronectin enhancement of corneal epithelial wound healing of rabbits in vivo," Arch. Ophthalmol., vol. 102, pp. 455–456 (1984).

Nishida, T. et al., "Fibronectin promotes epithelial migration of cultured rabbit cornea in situ," J. Cell Biol., vol. 97, p. 1653 (1983).

Nomizu, M. et al., "Identification of cell binding sites in the laminin alpha 1 chain carboxyl–terminal globular domain by systemic screening of synthetic peptides," J. Biol. Chem., vol. 270, pp. 20583–20590 (1995).

Parks, R.A. et al., "Hydrogel keratophakia: Long–term morphology in the monkey model," CLAO J., vol. 17(3), pp. 216–222 (1991).

Pettit, D.K. et al., "Correlation between corneal epithelial cell outgrowth and monoclonal antibody binding to the cell binding domain of adsorbed fibronectin," J. Biomed. Mater. Res., vol. 28, pp. 685–691 (1994).

Pettit, D.K. et al., "Influence of the substrate binding characteristics of fibronectin on corneal epithelial cell outgrowth," J. Biomed. Mater. Res., vol. 26, pp. 1259–1275 (1992).

Pettit, D.K. et al., "Quantitation of rabbit corneal epithelial cell outgrowth on polymeric substrates in vitro," Invest. Ophthalmol. Vis. Sci., vol. 31, pp. 2269–2277 (1990).

Phan, T.–M. et al., "Topical fibronectin in the treatment of persistent corneal epithelial defects and trophic ulcers," Am. J. Ophthalmol., vol. 104, pp. 494–501 (1987).

Pitt, W.G. et al., "Adsorption of fibronectin to polyurethane surfaces: Fourier transformed infrared spectroscopic studies," In: Brash JL, Horbett TA (eds), A CS Symposium Series 343, Proteins and Interfaces: Physicochemcial and Biochemical Studies, pp. 324–338 (1977).

Refojo, M.F. et al., "Tear protein adsorption on hydrogels: a possible cause of contact lens allergy," Contact & Intraolular Lens Medical Journal, vol. 3, (1), pp. 23–25 (1977).

Remes, A. et al., "Immune response in biocompatability", Biomaterials, vol. 13(11), pp. 731–740 (1992).

Rousselle, P. et al., "An epithelium–specific basement membrane adhesion molecule that is a Component of anchoring filaments," J. Cell Biol., vol. 114, pp. 567–576 (1991).

Sorokin, L.M. et al., "Developmental regulation of the laminin α5 chain suggests a role in epithelial and endothelial cell maturation," Dev.Biol., vol. 189, pp. 285–300 (1997).

Steele, J.G. et al., "Attachment of human bone cells to tissue culture polystyrene: the effect of surface chemistry upon initial cell attachment," J. Biomater. Sci. Polymer Edn., vol. 5, pp. 245–257 (1993).

Tashiro, K.–I. et al., "The RGD containing site of the mouse laminin A chain is active for cell attachment, spreading, migration and neurite outgrowth," J. Cell Physiol., vol. 146, pp. 451–459 (1991).

Thompson , K.P.et al., "Synthetic epikeratoplasty in rhesus monkeys with human type IV collagen," Cornea, vol. 12(1), pp. 35–45 (1993).

Thompson, K.P. et al., "Current status of synthetic epikeratoplasty," Refract. Corneal Surg., vol. 7, pp. 240–248 (1991).

Thompson, P. et al., "The effect of an eye–derived growth factor (EDGF) on corneal epithelial regeneration," Exp. Eye Res., vol. 34, pp. 191–199 (1982).

Trinkaus–Randall, V. et al., "Development of a biopolymeric keratoprosthetic material," Invest. Ophthalmol. Vis. Sci., vol. 29(3), pp. 393–400 (1988).

Truskey, G.A. et al., "Relationship between 3T3 cell spreading and the strength of adhesion on glass and silane surfaces," Biomaterials, vol. 14, pp. 243–254 (1993).

Watanabe, K. et al., "Mechanisms of persistent epithelial defect formation: peptide from the cell–domain (GRGDS) inhibits corneal epithelial cell migration," Ivest. Ophthalmol. Vis. Sci., vol. 29(suppl), p. 192 (1988).

Watanabe, K. et al., "Stimulatory effects of fibronectin and EGF on migration of corneal epithelial cells," Invest. Ophthalmol. Vis. Sci., vol. 28, p. 205 (1987).

Wedler, F.C. et al., "Soft contact lenses: formation of deposits," In: Biocompatibility in Clinical Practice, Vol 2, Williams DF (ed). CRC Press, Inc., Boca Raton, Florida, pp. 32–46 (1982).

Werblin, T.P. et al., "Synthetic keratophakia for the correction of aphakia," Ophthalmology, vol. 94, pp. 926–934 (1987).

Wilson, S.E. et al., "EGF, basic FGF and TGF beta–1 messenger RNA production in rabbit corneal epithelial cells," Invest. Opthalmol. Vis. Sci., vol. 33, pp. 1987–1995 (1992).

Wilson, S.E. et al., "Fibroblast growth factor–1 receptor messenger RNA expression in corneal cells," Cornea, vol. 12, pp. 249–254 (1993).

Wu, X. Y. et al., "Expression of integrin and organization of F–actin in epithelial cells depends on the underlying surface," Invest. Ophthalmol. Vis. Sci., vol. 35, pp. 878–890 (1994).

Xie, R.Z. et al., "Effects of biologically modified surfaces of synthetic lenticules on corneal epithelialization in vivo," Austl. N.Z. J. Ophthalmol., vol. 25(Suppl 1), pp. S46–S49 (1997).

Yasuda, H. et al., "The rate of adhesion of melanoma cells onto nonionic polymer surfaces," J. Biomed. Mater. Res., vol. 12, pp. 701–706 (1978).

Bergstrom, K. et al., "Reduction of fibrinogen adsorption on PEG–coated polystyrene surfaces," J. Biomed. Mater. Res., vol. 26, pp. 779–790 (1992).

Mooradian, D.L. et al, "Characterization of FN–C/H–V, a novel synthetic peptide from fibronectin that promotes rabbit corneal epithelial cell adhesion, spreading and motility," Invest. Ophthalmol. Vis. Sci., vol. 34, pp. 153–164 (1993).

Cameron, J.D. et al., "Rabbit corneal epithelial cell adhesion to proteolytic fragments and synthetic peptides of fibronectin," Invest. Ophthalmol. Vis. Sci., vol. 32 (suppl), p. 1072 (1991).

Kugo, K. et al., "Fibroblast attachment to Arg–Gly–Asp peptide–immobilized poly(gamma–methyl L–Glutamate)," J. Biomater. Sci., Polymer Edn., vol. 5, pp. 325–327 (1994).

Kuhl, P.R. et al., "Tethered epidermal growth factor as a paradigm for growth factor–induced stimulation from the solid phase," Nature Med., vol. 2, pp. 1022–1027 (1996).

Nishida, T. et al., "Synergistic effects of substance P with insulin–like growth factor–1 on epithelial migration of the cornea," J. Cell Physiol., vol. 169, pp. 159–166 (1996).

Olbrich, K.C. et al., "Surfaces modified with covalently–immobilized adhesive peptides affect fibroblast population motility," Biomaterials, vol. 17, pp. 759–764 (1996).

Päällysaho, T. et al., "Epithelial cell–substrate adhesion in the cornea: Localization of actin, talin, integrin and fibronectin," Exp. Eye Res., vol. 52, pp. 261–267 (1991).

Steele, J.G. et al., "Mechanism of initial attachment of corneal epithelial cells to polymeric surfaces," Biomaterials, vol. 18, pp. 1541–1551 (1997).

Trinkaus–Randall, V. et al., "Modification of polymers for synthesis by corneal epithelial cells," Invest. Ophthalmol. Vis. Sci., vol. 32(suppl), pp. 1072 (1991).

Wilson, S.E. et al., "Effect of epidermal growth factor, hepatocyte growth factor, and keratinocyte growth factor, on proliferation, motility and differentiation of human corneal epithelial cells," Exp. Eye Res., vol. 59, pp. 665–678 (1994).

Wilson, S.E. et al., "Epithelial injury induces keratocyte apoptosis: Hypothesized role for the interleukin–1 system in the modulation of corneal tissue organization and wound healing," Exp. Eye Res., vol. 62, pp. 325–337 (1996).

* cited by examiner

SURFACE MODIFICATIONS FOR ENHANCED EPITHELIALIZATION

The benefit of the Mar. 31, 2000 filing date of provisional application serial No. 60/193,528 is claimed under 35 U.S.C. §119(e).

The development of this invention was partially funded by the Government under grant RO1EV12367-01 awarded by the National Institute of Health. The Government has certain rights in this invention.

This invention pertains to a method and device to use certain enhancer molecules tethered to an artificial surface in such a manner that the molecules retain their quaternary structure and that the surface produced promotes normal corneal epithelialization.

The Corneal Epithelium

The cornea serves several important functions for vision, e.g., refracting >80% of the incoming light onto the retina, filtering out harmful UV rays, and maintaining an optical "window." The cornea is composed of five structural layers: the epithelium, Bowman's layer, stroma, Descemet's membrane, and endothelium. The outermost layer, the corneal epithelium, is a multi-layered structure with a complex arrangement of intercellular junctions, chemical signaling, and nerve endings. Similar to other epithelial layers throughout the body, the corneal epithelium prevents entry of pathogens, provides a barrier against fluid loss, and protects against abrasive wounding. The epithelium is separated from the external environment only by a layer of fluid, the tears.

The corneal epithelium is composed of three types of cells—the basal cells (1 layer), wing cells (1–3 layers), and squamous cells (3–4 layers)—which adhere to one another by tight cell junctions. The basal cells also form strong adhesion complexes with the underlying extracellular matrix and ultimately with Bowman's layer. Bowman's layer, the anterior-most layer of the corneal stroma, is an acellular zone consisting of collagen fibrils and associated proteoglycans which are densely woven in a random fashion into a felt-like matrix. Of the cells in the epithelium, only the basal cells have mitotic capabilities. Like all stratified epithelia in the body, the corneal epithelium is self-renewing; complete cellular turnover occurs every 5–7 days. Generally, after the basal cells undergo mitosis, the daughter cells begin to move outward toward terminal differentiation and eventual desquamation. See C. Hanna et al., "Cell production and migration in the epithelial layer of the cornea," Arch. Ophthalmol., vol. 64, pp. 536 (1960).

Epithelial Cell Migration During Wound Healing

Natural corneal epithelialization occurs in response to a wound. Epithelial recovery following an external injury is a complex process characterized by two phases, the latent phase and the healing phase. See C. E. Crosson et al., "Epithelial wound closure in the rabbit cornea: A biphasic process," Invest. Ophthalmol. Vis. Sci., vol. 21, pp. 464–473 (1986). These phases are thought to be initiated by the immediate expression of a nucleoprotein-encoding protooncogene (c-fos). Immediately after full-thickness wounding, the damaged cells adjacent to the wound edge lose surface microvilli. Polymorphonuclear neutrophils (PMNs) arrive via the tear film and begin the process of debriding cellular remnants. During the first six hours of epithelial debridement (latent phase), a single layer of epithelial cells at the wound margin becomes motile by forming cellular processes at the wound edge and releasing their hemidesmosomal attachments to the basement membrane. Fibronectin, the glycoprotein widely involved in cell-to-cell and cell-to-substrate interactions, is deposited from the tears onto the denuded corneal surface, along with fibrinogen and fibrin. See L. S. Fujiikawa et al., "Fibronectin in healing rabbit cornea wounds," Lab. Invest., vol. 45, pp. 120 (1981).

The initiation of lateral migration of epithelial cells over the wound signifies the onset of the healing phase. In association with the proteins fodrin and vinculin, the assembly and disassembly of intracellular actin filaments provides cytoskeletal locomotive support during this pre-mitotic stage of the healing phase. Adhesion of the migrating epithelial monolayer to the stroma is thought to be mediated by the glycoprotein fibronectin. See S. Hiraki et al., "Biochemical and histological findings on the effect of fibronectin in rabbits with experimental corneal disorders," Arzneim-Forch/Drug Res., vol. 40, pp. 1336–1340 (1990). Fibronectin contains both cell-specific binding sequences and a binding region for heparin sulfate and type IV collagen (basement membrane components). Fibronectin is thought to provide a temporary subepithelial matrix on which the epithelial cells can migrate, in repetitive cycles during which the cells cleave their attachments, advance, and then form new attachments. Plasmin, generated by urokinase-like plasminogen activator (uPA), is thought to cleave the fibronectin at the basal cell surface to release the leading edge of the epithelium. See M. Berman, "The pathogenesis of corneal epithelial defects," In *Healing Processes in the Cornea*, (Beuerman et al. eds), Portfolio Publishing Company, The Woodlands, Tex. (1989). After about 24 hours, the migrating epithelial cells begin to proliferate, and the epithelium attaches to the basement membrane more firmly via newly synthesized hemidesmosomes and associated type VII collagen containing anchoring filaments. See I. K. Gipson et al., "Anchoring fibrils form a complex network in human and rabbit cornea," Invest. Ophthalmol. Vis. Sci., vol. 28, pp. 212–220 (1987). The anchoring filaments pass through the basement membrane and are contiguous with anchoring fibrils that terminate as anchoring plaques in Bowman's layer. See I. K. Gipson et al., 1987; and T. Nishida et al., "Expression of fibronectin receptors in corneal epithelial cells," In: Healing Processes in the Cornea (Beuerman R W, Crosson C E, Kaufman H E (eds)), Portfolio Publishing Company, The Woodlands, Tex. (1989). The proteins laminin, K-laminin, talin, integrin, and kalinin also play roles in the attachment of the epithelium to the stroma. See L. M. Sorokin et al., "Developmental regulation of the laminin $\alpha 5$ chain suggests a role in epithelial and endothelial cell maturation," Dev. Biol., vol. 189, pp. 285–300(1997); L. S. Grushkin-lerner et al., "Expression of integrin receptors on plasma membranes of primary corneal epithelial cells is matrix specific," Exp. Eye Res. vol. 64, pp. 323–334 (1997); M. P. Marinkovich et al., "The dermal-epidermal junction of human skin contains a novel laminin variant," J. Cell Biol., vol. 119, pp. 696–703 (1992); A. Horowitz et al., "Interaction of plasma membrane fibronectin receptor with talin: a transmembrane linkage," Nature, vol. 320, pp. 531–533 (1986); T. Paallysaho et al., "Epithelial cell-substrate adhesion in the cornea: Localization of actin, talin, integrin and fibronectin," Exp. Eye Res., vol. 52, pp. 261–267 (1991); and P. Rousselle et al., "An epithelium-specific basement membrane adhesion molecule that is a component of anchoring filaments," J. Cell Biol., vol. 114, pp. 567–576 (1991).

Although much is known about the factors that make up the adhesion complexes, the precise sequence by which these adhesion complex components are assembled is still unknown. Certain growth factors, such as EGF, FGF, and TGF-$\beta$, enhance the rate of epithelial wound healing, and human epithelial growth factor (EGF) has been specifically shown to induce a dose-dependent increase in epithelial replication in the epithelial stem cells of the corneoscleral limbus. See M. Grant et al., "Effects of epidermal growth factor, and transforming growth factor-β on corneal cell chemotaxis," Invest. Ophthalmol. Vis. Sci., vol. 33, pp. 3292–3301 (1992); S. E. Wilson et al., "Fibroblast growth factor-1 receptor messenger RNA expression in corneal cells," Cornea, vol. 12, pp. 249–254(1993); and S. E. Wilson et al., "EGF, basic FGF and TGF beta-1 messenger RNA production in rabbit corneal epithelial cells," Invest. Opthalmol. Vis. Sci., vol. 33, pp. 1987–1995 (1992).

Both laminin and fibronectin are multifunctional extracellular matrix proteins that play a central role in cell adhesion and migration. Expression of integrin receptors for both of these proteins has been shown to occur within hours of the ligands being detected in the matrix. See L. S. Grushkin-Lerner et al., "Expression of integrin receptors on plasma membranes of primary corneal epithelial cells is matrix specific," Exp. Eye Res., vol. 64, pp. 323–334 (1997). Laminin is a major component of the intact basal lamina and has been shown to enhance epithelial cell adhesion and spreading on surfaces. See V. Trinkaus-Randall et al., "Modification of polymers for synthesis by corneal epithelial cells," Invest. Ophthalmol. Vis. Sci., vol. 32(suppl), pp. 1072 (1991). In the cornea, fibronectin is seen on the surface of healing epithelial wounds. See L. S. Fujikawa et al., "Fibronectin in healing rabbit corneal wounds," Lab. Invest., vol. 45, p. 120 (1981). Exogenous fibronectin has been shown to promote the healing of corneal epithelial wounds in vivo and in vitro and the healing of persistent corneal epithelial defects in humans. See T. Nishida et al., "Fibronectin enhancement of corneal epithelial wound healing of rabbits in vivo," Arch. Ophthalmol., vol. 102, pp. 455–456 (1984); and K. Watanabe et al., "Stimulatory effects of fibronectin and EGF on migration of corneal epithelial cells," Invest. Ophthalmol. Vis. Sci., vol. 28, p. 205 (1987).

Substance P is a corneal neurotransmitter. The cornea is heavily innervated with sensory nerve fibers. This innervation plays an important role in the maintenance of the normal structure and functions of the cornea and in the wound healing process. In clinical settings, patients who suffer from delayed epithelial wound healing or persistent corneal epithelial defects have decreased corneal sensitivity, which suggests impairment of the sensory nerve fibers. Recently a synergistic effect of substance P and IGF-1 on the stimulation of rabbit corneal epithelial cell migration and attachment to extracellular matrix proteins has been reported. See T. Nishida et al., "Synergistic effects of substance P with insulin-like growth factor-1 on epithelial migration of the cornea," J. Cell Physiol., vol. 169, pp. 159–166 (1996).

If the epithelial basement membrane has not been damaged by the injury, the recovering epithelial cells are able to use it for tight adhesion to the underlying stroma, as evidenced by the reappearance of hemidesmosomes two days after injury and by tight adhesion shortly thereafter. See A. A. Khodadoust et al., "Adhesion of regenerating corneal epithelium: the role of basement membrane," Am. J. Ophthalmol., vol. 65, pp. 339–348 (1968). However, if the basement membrane has been damaged, new basement membrane complexes do not begin to form until five to seven days after injury. Depending on the severity of the basement membrane damage, complete basement membrane reconstruction may take as long as nine weeks.

Recently, investigators have hypothesized that if the epithelial injury penetrates the basement membrane, such as in refractive corneal surgery, programmed cell death (apoptosis) in the underlying anterior stromal keratocytes is stimulated. Apoptosis of the keratocytes immediately after a deep epithelial injury may be mediated by modulators, such as interleukin-1 alpha and beta, that are released from injured or dead corneal epithelial cells. See S. E. Wilson et al, "Epithelial injury induces keratocyte apoptosis: Hypothesized role for the interleukin-1 system in the modulation of corneal tissue organization and wound healing," Exp. Eye Res., vol. 62, pp. 325–337 (1996). The subsequent stromal wound healing response is not limited to production of collagen and other components of stromal remodeling by activated keratocytes as they repopulate the anterior corneal stroma. Activated keratocytes also secrete hepatocyte growth factor (HGF) and keratinocyte growth factor (KGF), the effects of which are not restricted to the stromal cells. These growth factors also stimulate epithelial cell proliferation and inhibit epithelial differentiation, effects that could promote epithelial hyperplasia and ultimately prolong the entire wound healing response. See S. E. Wilson et al., "Effect of epidermal growth factor, hepatocyte growth factor, and keratinocyte growth factor, on proliferation, motility and differentiation of human corneal epithelial cells," Exp. Eye Res., vol. 59, pp. 665–678 (1994).

Corneal Augmentation and Replacement

Complete synthetic replacement of diseased or opacified corneas has been investigated for more than 200 years. While initial replacement studies included the use of glass, metal, and bone as substitute materials, studies over the past 50 years have focused on the use of polymers. As the field of polymer chemistry and the understanding of its medical applications has grown, there has been a shift from the use of nonporous, rigid polymers such as polymethyl methacrylate (PMMA) to more pliable polymers, such as collagen, polyurethanes, poly(2-hydroxyethylmethacrylate) polyglycerolmethacrylate, polyvinyl alcohol, polyethylene glycol, polymethacrylic acid, silicones, polyfluorocarbons and co-polymers thereof. See U.S. Pat. No. 4,865,601; J. T. Jacob-LaBarre et al., "Development of a new type of artificial cornea for treatment of endstage corneal diseases," Progress in Biomedical Polymers, C G Gebelein and R L Dunn (eds.), Plenum Press, New York (1990); V. Trinkaus-Randall et al., "Development of a biopolymeric keratoprosthetic material," Invest. Ophthalmol. Vis. Sci., vol. 29(3), pp. 393–400 (1988); G. J. Crawford et al., "Preliminary evaluation of a hydrogel core-and-skirt keratoprosthesis in the rabbit cornea," J. Refract. Surg., vol. 12, pp. 525–529 (1996); D. Dupont et al., "Biocompatibility of human collagen type IV intracorneal implants," Cornea, vol. 8(4), pp. 251–258 (1989); W. H. Beekhuis et al., "Complications of hydrogel intracorneal lenses in monkeys," Arch. Ophthalmol., vol. 105, pp. 116–122 (1987).

Recently there have been reports of success in both corneal augmentation and replacement. For replacement devices, the use of a soft, porous polymer attachment skirt has improved anchoring of the central optic and decreased extrusion of the devices. See J. T. Jacob-LaBarre et al., "Development of a practical artificial cornea for end stage corneal diseases," Transactions. Thirteenth Annual Meeting for the Society for Biomaterials, New York City, Volume X, p. 57 (1987); J. T. Jacob-LaBarre et al., "Development of a soft artificial cornea for end stage corneal diseases," Proceedings of the American Chemical Society Division of Polymeric Materials: Science and Engineering, Los Angeles, Volume 59, pp 95–99 (1988); and C. J. Crawford et al., "Tissue interaction with hydrogel sponges implanted in the rabbit cornea," Cornea, vol. 12(4), pp. 348–357 (1993). For augmentation devices, the use of hydrogels that allow nutrients to permeate the material to supply the tissue anterior to the implant have significantly increased the functional life of the devices. See K. P. Thompson et al., "Current status of synthetic epikeratoplasty," Refract. Corneal Surg., vol. 7, pp. 240–247 (1991). Both types of devices share the requirement that corneal epithelial cells be able to form a viable confluent layer across the anterior surface of the optical material. However, success in that area has been limited. Although a few replacement materials have shown short-term success in maintaining a somewhat normal epithelial layer (basically a tri-cellular multilayer sheet), long-term analysis (up to 8 years) has shown that the density of the epithelial layer is not maintained. See R. A. Parks et al., "Hydrogel keratophakia: Long-term morphology in the monkey model," CLAO J., vol. 17(3), pp. 216–222 (1991); and T. P. Werblin et al., "Synthetic keratophakia for the correction of aphakia," Ophthalmology, vol. 94, pp. 926–934 (1987).

Polymers in Biological Environments

When a synthetic material is placed in a biological environment, its surface interacts with the surrounding biological molecules. The proteins and minerals contained in the contacting interstitial fluids, such as synovial, lymphatic, or extracellular fluids, as well as blood and tears, can react specifically and non-specifically with the material surface. Over the past 30 years, extensive efforts have been made to determine the factors influencing these reactions. On a macro level, the physical characteristics of the material in relation to those of the surrounding environment (e.g., rigidity versus softness) play a critical role. Also, surface characteristics such as roughness versus smoothness influence not only fluid flow patterns and shear rates, but also the adherence of clots and cells. See S. D. Bruck, "Physicochemical aspects of the blood compatibility of polymer surfaces," J. Polymer Sci., Polymer Symp., vol. 66, pp. 283 (1979). On a micro level, the degree of ionization and solvation of the surface and solutes and the concentration of the solutes in the surrounding media are important. The interfacial surface energy of the material also plays an important role in the thermodynamic free energy of adhesion for solutes in the surrounding media in the absence of any specific biochemical interactions (i.e., ligand-receptor interactions). See M. N. Helmus, "The effect of surface charge on arterial thrombosis," J. Biomed. Mater. Res., vol. 18, p. 165 (1984); and D. J. Lymann et al., "The effect of chemical structure and surface properties of polymers on the coagulation of blood. I. Surface free energy effects," Transact. Am. Soc. Artific. Intern. Organs., vol. XI, pp. 301–306 (1965).

Generally, proteins are intrinsically surface-active and tend to concentrate at interfaces, in part because of their polymeric structure and in part because of their typically amphoteric nature. The opportunity for multiple modes of binding with many different types of surfaces is provided by the polar, charged, and nonpolar amino acid side chains of the proteins. It has been observed that the general tendency for nonpolar residues to be internalized in the native protein often causes structural alterations of the protein upon adsorption, to maximize the number of contacts with the surface. See A. S. Hoffman, "Blood-biomaterial interactions: an overview," In: Biomaterials: Interfacial Phenomena and Applications, (S. L. Cooper and N. A. Peppas (eds)), Advances in Chemistry Series 199, p. 3 (1982). Real-time FTIR analysis of proteins binding to surfaces has demonstrated conformational changes in the proteins as they first adhere and then adsorb to the material surface. See E. J. Castillo et al., "Protein adsorption on hydrogels. II. Reversible and irreversible interactions between lysozyme and soft contact lens surfaces," Biomaterials, vol. 6, pp. 338–344 (1985); and E. J. Castillo et al., "Characterization of protein adsorption on soft contact lenses. I. Conformational changes of adsorbed human serum albumin," Biomaterials, vol. 5, pp. 319–325 (1984).

There are at least two different processes for the deposition and binding of proteins on surfaces: non-selective adsorption and the Vroman effect. Non-selective adsorption is based on initial polar interactions between the surface and the solutes. Specifically, for a hydrophilic hydrogel surface in a physiological medium (e.g., a soft contact lens in the tear fluid), metal ions in the hydrating fluid, such as $Ca^{2+}$ and $Mg^{2+}$, first interact and bind to the hydrogel matrix. The initial binding of proteins and lipids to the surface then occurs either through the polar side-chain groups of proteins or the polar head groups of the lipids, with the metal cations and hydrogel surface pendant groups acting as chelation or nucleation sites for the polar protein and lipid binding. Body beat, conformational changes, and the natural dehydration forces of hydrogen bond formation denature the proteins and lipids bound to the surface, resulting in a very thin layer of strongly bound and conformationally altered protein at the interfacial surface. Additional proteins and lipids arriving at the surface then bond with the exposed groups of the bound proteins and lipids. The new proteins are weakly bound to the first surface layer of proteins, with minimal conformational changes. Subsequent proteins and lipids become loosely associated with the weakly bound proteins, with no conformational changes. The proteins in the top layers of the adsorbed protein interact only with each other, never "seeing" the hydrogel surface. See Castillo, 1985; and J. L. Bohnert et al., "Adsorption of proteins from artificial tear solutions to contact lens materials," Invest. Ophthalmol. Vis. Sci., vol. 29, pp. 362–373 (1988).

The Vroman effect proposes that protein-surface interactions in vivo (or in vitro from mixed solutions) occur as a succession of events. Molecules with low molecular weight and in high concentrations arrive first. Later, high molecular weight proteins in low concentrations displace the early arrivals. Even after the total surface concentration of protein reaches a steady state, the composition of the protein film may continue to change, with later arriving proteins eventually dominating the composition of the protein film. In this way, the surface may selectively adsorb a specific protein type or conformation. See F. C. Wedler et al., "Soft contact lenses: formation of deposits," In: Biocompatibility in Clinical Practice, Vol 2, Williams D F (ed). CRC Press, Inc., Boca Raton, Fla. (1982); and C. A. LeDuc et al., "A mathematical model for the Vroman effect," Ind. Eng. Chem. Res., vol. 34, pp. 3488–3495 (1995).

Once the adsorbed protein layer forms, the interactions of the biomaterial with the biological environment are mediated through this proteinaceous layer. The composition of the protein layer and the conformation and binding strength of the adsorbed proteins depend on both the surface properties of the material and the properties of the proteins present in the biological environment. See T. A. Horbett, "The role of adsorbed proteins in animal cell adhesion," Colloids and Surfaces B: Biointerfaces, vol. 2, pp. 225–240 (1994). Different biological responses occur with different synthetic materials because the adsorbed protein layer can be different in each case, even when the biological environment is the same. Therefore, cells approaching the surface of a synthetic material initiate a foreign body reaction mainly in response to the characteristics of the adsorbed protein layer, unless they recognize the protein layer as "self."

Recognition of the protein layer as "self" is mediated by complement factors in the interstitial fluids. Although the specific sequence of protein adherence to different polymer surfaces in vivo has not been elucidated, activation of complement component C3b at the material surface has been identified.

See C. P. Klein et al., "Activation of complement C3 by different calcium phosphate powders," Biomaterials, vol. 4, pp. 181–184 (1986). Once activated, C3b (either surface-bound or free) can interact directly with macrophages and indirectly with T cells by several mechanisms to initiate a foreign body response. Bound C3b can mediate macrophage attachment to the material's surface. (Macrophage adhesion leads to the release of lysosomal enzymes and other cytotoxic components from the macrophages.) The intensity or degree to which the foreign body response is maintained at the material's surface determines the ability of healthy cells to proliferate and spread on or near that surface. See A. Remes et al., "Immune response in biocompatability," Biomaterials, vol. 13(11), pp. 731–743 (1992).

Cell Adhesion to Polymers

Cell adhesion to a material, whether that material is the naturally occurring extracellular matrix (ECM) of the basement membrane or a synthetic biomaterial, is mediated primarily by the interaction between surface-bound proteins and the corresponding receptors on the cell membrane. Many years of biomaterial research have focused on optimizing the material surface characteristics, such as charge, energy, and roughness, to influence specific protein deposition, to try to tailor the Vroman effect for the specific type of cellular adhesion desired. Studies involving both fibroblasts and endothelial cells in culture have shown that positively charged surfaces enhance cell proliferation and adhesion significantly better than negatively charged or non-ionic hydrogel surfaces. See S. Hattori et al., "Fibroblast cell proliferation on charged hydroxyethyl methacrylate copolymers," J. Colloid Interface Sci., vol. 104, pp. 72–78 (1985); and X. Y. Wu et al., "Expression of integrin and organization of F-actin in epithelial cells depends on the underlying surface," Invest. Ophthalmol. Vis. Sci., vol. 35, pp. 878–890 (1994). High surface energy or wettability has been shown to interfere with both human fibroblast and endothelial cell attachment, and low surface energy or wettability has been shown to interfere with plasma protein adsorption. See H. Yasuda et al., "The rate of adhesion of melanoma cells onto nonionic polymer surfaces," J. Biomed. Mater. Res., vol. 12, pp. 701–706 (1978); and G. Altankov et al., "Reorganization of substratum on hydrophilic and hydrophobic materials is related to biocompatibility," J. Mater. Sci., vol. 5, pp. 732–737 (1994). In general, non-wettable materials have been shown to inhibit the attachment and growth of anchorage-dependent cells. See T. Groth et al., "Studies on cell-biomaterial interaction: role of tyrosine phosphorylation during fibroblast spreading on surfaces varying in wettability," Biomaterials, vol. 17, pp. 1227–1234 (1996). Recent studies have shown that microscopically roughened surfaces demonstrate enhanced vascular cell adhesion and migration rates, compared with smooth surfaces of the same material. See M. Lampin et al., "Correlation between substratum roughness and wettability, cell adhesion, and cell migration," J. Biomed. Mater. Res., vol. 36, pp. 99–108 (1997); and S. L. Goodman et al., "Three-dimensional extracellular matrix textured biomaterials," Biomaterials, vol. 17, pp. 2087–2095 (1996).

Further research has indicated the importance of the conformation of the protein in promoting interaction with cells. Studies have shown that extracellular matrix proteins such as fibronectin and vitronectin must be adsorbed from the plasma or serum onto biomaterial surfaces as a prerequisite for successful cell adhesion and spreading. See J. G. Steele et al., "Attachment of human bone cells to tissue culture polystyrene: the effect of surface chemistry upon initial cell attachment," J. Biomater. Sci. Polymer Edn., vol. 5, pp. 245–257 (1993). However, adsorption of fibronectin onto hydrophobic materials is followed by a decrease in cell adhesion, adhesion strength, and diminished cell spreading, a fact that has been attributed to the possible conformation changes in the protein induced upon adsorption. See D. J. Juliano et al., "Effect of the conformation and orientation of adsorbed fibronectin on endothelial cell spreading and the strength of adhesion," J. Biomed. Mater. Res., vol. 27, pp. 1103–1113 (1993); and J. D. Andrade et al., "Protein adsorption and materials biocompatibility: A tutorial review and suggested hypothesis," Prog. Surface Sci., vol. 79, pp. 1–64 (1986). This phenomenon spurred investigators to pre-adsorb different proteins onto surfaces and determine the cellular response. Collagen, laminin, vitronectin, fibronectin, and albumin have been pre-adsorbed onto a variety of surfaces in an attempt to find appropriate binding substrates. See R. Z. Xie et al., "Effects of biologically modified surfaces of synthetic lenticules on corneal epithelialization in vivo," Austl. N.Z.J. Ophthalmol., vol. 25(Suppl 1), pp. S46–S49 (1997); S. M. Kirkham et al., "The keratoprosthesis: improved biocompatibility through design and surface modification," Ophthalmic Surg., vol. 22, pp. 455–461 (1991); V. Trinkaus-Randall et al., "Modification of polymers for synthesis by corneal epithelial cells," Invest. Ophthalmol. Vis. Sci., vol. 32(suppl), pp. 1072 (1991); and J. G. Steele et al., "Mechanism of initial attachment of corneal epithelial cells to polymeric surfaces," Biomaterials, vol. 18, pp. 1541–1551 (1997). Additionally, increased amounts of absorbed fibronectin are accompanied by decreased recognition of the cell-binding domain. See D. K. Pettit et al., "Correlation between corneal epithelial cell outgrowth and monoclonal antibody binding to the cell binding domain of adsorbed fibronectin," J. Biomed. Mater. Res., vol. 28, pp. 685–691 (1994). It has also been reported that cells are able to reorganize and rearrange adsorbed fibronectin on a hydrophilic glass surface but not on a hydrophobic surface. Cells can also increase the concentration of fibronectin on the surface beneath the cells. See G. Altankov et at, "Reorganization of substratum-bound fibronectin on hydrophilic and hydrophobic materials is related to biocompatibility," J. Mater. Sci. Mater. Med., vol. 5, pp. 732–737 (1994). Tyrosine phosphorylation in fibroblasts on surfaces of varying wettability has been examined, and the studies indicated that the adverse effect of hydrophobic surfaces on cell adhesion and proliferation was due to an impaired transfer of signals via integrins from the substratum (adsorbed fibronectin) to the cell interior. See T. Groth et al., "Studies on cell-biomaterial interaction: role of tyrosine phosphorylation during fibroblast spreading on surfaces varying in wettability," Biomaterials, vol. 17, pp. 1227–1234 (1996).

Tissued Engineered Surfaces

To improve cell adhesion and spreading, short peptide sequences, e.g., YIGSR and RGD, that are responsible for cell-surface adhesion binding activity in extracellular adhesion proteins (fibronectin and laminin) have been chemically incorporated onto polymer surfaces. See S. P. Massia et al., "Covalent surface immobilization of Arg-Gly-Asp- and Tyr-Ile-Gly-Ser-Arg-containing peptides to obtain well-defined cell-adhesive substrates," Analyt. Biochem., vol. 187, pp.

292–301 (1990); S. P. Massia et al., "Covalently immobilized laminin peptide Tyr-Ile-Gly-Ser-Arg (YIGSR) supports cell spreading and co-localization of the 67-kilodalton laminin receptor with α-actinin and vinculin," J. Biol. Chem., vol. 268, pp. 8053–8059 (1993); H.-B. Lin et al, "Synthesis, surface, and cell-adhesion properties of polyurethanes containing covalently grafted RGD-peptides," J. Biomed. Mater. Res., vol. 28, pp. 329–342 (1994); and J. R. Glass et al., "Characterization of a hyaluronic acid-Arg-Gly-Asp peptide cell attachment matrix," Biomaterials, vol. 17, pp. 1101–1108 (1996). Although these minimal binding sequences have only a fraction of the activity of the entire protein, their small size allows them to be incorporated at much higher concentrations than would be possible with entire proteins. The short peptide sequences have the advantage of being relatively stable, and their synthetic nature renders them amenable to chemical derivatization and covalent attachment.

Direct attachment of these cell-surface receptor recognition sequences has been associated with an increase in cell culture adhesion for a variety of cell types, including human foreskin fibroblasts, bovine pulmonary endothelial cells, human umbilical vein endothelial cells, and porcine pulmonary aortic endothelial cells. See the references cited in the preceding paragraph. However, the increase in cell adhesion response in these systems, while significant, was not as high as had been hoped, and the adhesion levels did not reach those seen in natural systems. Generally, the increase seemed to be of a nonspecific nature and was not found for all cell types tested. See D. L. Hern et al., "Incorporation of adhesion peptides into nonadhesive hydrogels useful for tissue resurfacing," J. Biomed. Mater. Res., vol. 39, pp. 266–276 (1998). Use of these sequences on surfaces cultured with rabbit corneal epithelial cells has not demonstrated the same marked increase in cell adhesion as has been reported for other cellular systems. See V. Trinkhaus-Randall et al., 1991; and K. Watanabe et al., "Mechanisms of persistent epithelial defect formation: peptide from the cell-domain (GRGDS) inhibits corneal epithelial cell migration," Invest. Ophthalmol. Vis. Sci., vol. 29(suppl), p. 192 (1988). More recently, the fibronectin adhesion-promoting peptide sequence, H-trp-gln-pro-pro-arg-ala-arg-ile-OH, (FAP), a peptide encompassing the heparin binding domain of the fibronectin molecule has shown some ability to increase corneal epithelial cell proliferation. See D. L. Mooradian et al, "Characterization of FN-C/H-V, a novel synthetic peptide from fibronectin that promotes rabbit corneal epithelial cell adhesion, spreading and motility," Invest. Ophthalmol. Vis. Sci., vol. 34, pp. 153–164 (1993).

Other research has shown that attaching a peptide sequence to a spacer arm resulted in a 50% increase in specific cell attachment, compared with the response to a surface with directly attached peptides. See K. Kugo et al., "Fibroblast attachment to Arg-Gly-Asp peptide-immobilized poly(gamma-methyl L-Glutamate)," J. Biomater. Sci., Polymer Edn., vol. 5, pp. 325–327 (1994); and D. L. Hern et al., 1998. However, other research has indicated that cell adhesion proteins have multiple attachment sites. Five peptide sequences on the laminin alpha 1 chain carboxyl-terminal globular domain have been found to exhibit cell-type-specific attachment activities, including SIYITRF, IAFQRN, and LQVQLSIR. See M. Nomizu et al., "Identification of cell binding sites in the laminin alpha 1 chain carboxyl-terminal globular domain by systemic screening of synthetic peptides," J. Biol. Chem., vol. 270, pp. 20583–20590 (1995). PHSRN, a synergistic peptide that enhances the activity of the RGD peptide, has been found in the central cell-adhesive domain of fibronectin. See S. Aota et al., "The short amino acid sequence Pro-His-Ser-Arg-Asn in human fibronectin enhances cell-adhesive function," J. Biol. Chem., vol. 269, pp. 24756–24761 (1994). Additionally, in rabbit corneal epithelial cells an interaction between cells and fibronectin via multiple adhesion-promoting sequences within the intact fibronectin molecule was shown. See J. D. Cameron et al., "Rabbit corneal epithelial cell adhesion to proteolytic fragments and synthetic peptides of fibronectin," Invest. Ophthalmol. Vis. Sci., vol. 32(suppl), pp. 1072 (1991).

Recently investigators have reported the use of tethering biologically active molecules to polymer scaffolds for tissue regeneration. See L. Griffith Cima, "Polymer substrates for controlled biological interactions," J. Cell. Biochem., vol. 56, pp. 155–161 (1994); and P. R. Kuhl et al., "Tethered epidermal growth factor as a paradigm for growth factor-induced stimulation from the solid phase," Nature Med., vol. 2, pp. 1022–1027 (1996). By covalently linking epithelial growth factor (EGF) onto a star-poly(ethylene oxide) (PEO) tether and then anchoring the tether onto the surface of a biodegradable scaffold, a 40% increase in rat hepatocyte cell adhesion and migration was shown. See L. Griffith-Cima, "Tissue engineered scaffolds for liver regeneration," Presented at Molecular Engineering of Polymers workshop: Directing Biological Response, American Chemical Society, November, 1996. Moreover, it was also shown that DNA synthesis within the cells was comparable to the levels found when the medium contained free EGF.

U.S. Pat. No. 5,986,043 discloses photopolymerizable biodegradable hydrogels for use in reducing the formation of cell adhesion after surgery, in applying a drug locally to a tissue surface, and in adhering tissue surfaces in a patient.

U.S. Pat. No. 5,906,828 discloses growth effector molecules, including growth factors and extracellular matrix molecules, flexibly linked by branched tethers to a support medium; and the use of the combination to stimulate and support cell and tissue growth.

U.S. Pat. No. 5,836,313 discloses a two-layer composite material composed of a thin-layer tissue and a hydrogel which is designed to provide a suitable substrate for corneal epithelial cell growth while maintaining the clarity, flexibility, and diffusivity of hydrogels.

U.S. Pat. Nos. 5,830,504 and 5,654,267 disclose a composition of an $\alpha_v\beta_3$ integrin ligand and a growth factor receptor ligand combined in a matrix that was said to be useful for promoting wound healing and tissue regeneration.

U.S. Pat. Nos. 5,760,176 and 5,120,829 disclose a method to attach a peptide to a solid substrate using its hydrophobic domains.

U.S. Pat. No. 5,716,633 discloses a collagen-hydrogel fabricated into an artificial lens which is capable of promoting epithelial cell growth.

U.S. Pat. No. 5,677,276 discloses peptides conjugated to hyaluronate polymers which may be used to promote the healing of wounds and tissue regeneration.

U.S. Pat. No. 5,512,474 discloses a cell culture system which comprises a support material with a surface bearing a combination of a positively-charged molecule and a cell adhesion factor.

U.S. Pat. No. 5,278,063 discloses a method to chemically graft peptides to a surface to enhance cell-surface adhesion to optimize cell culture systems and to improve cell bioadhesion to surfaces made of various materials.

U.S. Pat. No. 5,171,264 discloses hydrogels produced by covalently immobilizing polyethylene oxide star molecules onto a support surface.

Attempts to augment and replace the cornea with synthetic materials that preferably have a refractive index close to that of the normal cornea have met with limited success primarily because these devices have been unable to support and maintain a normal stratified epithelium as an effective barrier. The fundamental problem is that the host epithelial cells recognize the polymer surface as other than the normal stroma layer or "self," triggering an immunological response throughout the life of the implant. Although some surfaces have shown a degree of epithelial growth, the resulting epithelium has been irregular, lacking the normal tri-layer appearance.

We have developed a synthetic device for cornea augmentation and replacement that increases corneal epithelium cell adhesion and migration. Additionally, the device can be used to improve vision. By using tethered corneal enhancer molecules, for example, extracellular matrix proteins (ECMPs), corneal growth factors, and other ligand-specific enhancer molecules on the surface of an optical polymer for use as corneal device, the epithelial cell response can be significantly enhanced for the following reasons: a) the tethers (or chains) hold the corneal enhancer molecules to the surface in a favorable conformational state; and b) the tethers hold the corneal enhancer molecules far enough away from the surface that they are not obscured by non-specific protein binding to the surface. By tethering a combination of corneal enhancer molecules, a more natural environment can be created. Additionally, the surface topography of the artificial surface, preferably a hydrogel, can be micro-molded, lathed, or engineered prior to tethering the corneal enhancer molecules to resemble the natural underlying surface of the corneal epithelial cells, Bowman's layer. This system allows epithelial cells to spread and attach faster than existing systems, as well as providing an underlying textured surface that allows the cells to resist the shear force induced in vivo by the blinking of the eyelid. Moreover, the resulting epithelial layer closely resembles a natural epithelial layer. The material can be used, for example, as a corneal onlay, an epikeratophakia lenticule, an intracorneal augmentation device, or an artificial cornea.

As used in the specification and claims, "optical polymer" refers to a device or part of a device which can be manufactured to be used to augment or replace the natural cornea. Preferably the optical polymer has a refractive index close to that of a natural cornea. Examples of polymers useful in making an optical polymer include collagen, polyurethanes, poly(2-hydroxyethylmethacrylate), polyglycerolmethacrylate, polyvinylpyrolidone, polyvinyl alcohol, polyethylene glycol, polymethacrylic acid, silicones, polyfluorocarbons, polymers with phosphocholine groups and co-polymers or combinations thereof. Some of these polymers will form a surface with reactive chemical species to which a tether can attach. Other polymers will need to have the surface treated by methods known in the art to produce reactive species for linkage of the tether, for example, by plasma etching, ion beam, corona discharge, electron beam, ion exchange, UV irradiation, or gamma irradiation.

As used in the specification and claims, "tether" refers to a polymer or chain of chemical molecules that serves as a link between the surface of the optical polymer and a corneal enhancer molecule. The tether is preferably a linear, single chain polymer for example, such as polyethylene oxide (PEO), without any significant pendant groups. The linear, single chain tether may also be made from amino acids or peptides. The molecular weight of the tether is preferably from about 2000 to about 8000, and most preferably about 3400. The tethers are covalently linked to the surface of the optical polymer and while these bonds are preferably hydrolyzable, they can be non-hydrolyzable in nature. The form depends on the tether material and the surface of the optical polymer.

As used in the specification and claims, "corneal enhancer molecule" refers to a biological molecule that binds to a corneal epithelial cell receptor and promotes the growth and expansion of the corneal epithelial cell layer. Corneal enhancer molecules include extracellular matrix proteins, corneal growth factors, and other ligand-specific corneal enhancer species that promote corneal epithelium growth and migration. Examples of extracellular matrix proteins include fibronectin, laminin, kalinin, K-laminin, vitronectin, talin, integrin, and albumin. Examples of corneal growth factors include insulin-like growth factor (IGF), fibroblast growth factor (FGF), hepatocyte growth factor, epithelial growth factor (EGF), transforming growth factor-$\alpha$ (TGF-$\alpha$), transforming growth factor-$\beta$ (TGF-$\beta$), keratinocyte growth factor (KGF), heparin binding factor, and nerve growth factor. Examples of other ligand-specific corneal enhancer species include the neurotransmitter, substance P; the cytokines, interleukin-1 alpha, and interleukin-1 beta; and peptides, including fibronectin adhesion-promoting peptide sequence consisting of H-trp-gln-pro-pro-arg-ala-arg-ile-OH, YIGSR, SIYITRF, PHSRN, IAFQRN, and LQVQL-SIR.

The effects of tethered corneal enhancer molecules on rabbit epithelial cell proliferation and adhesion have been measured. Tethers of 3400 MW poly(ethylene glycol) (PEG) (also known as polyethylene oxide, PEO) have been used to attach specific factors and proteins to a hydrogel surface. PEG does not interact with most macromolecules found in body fluids. For example, see K. Bergstrom et al., "Reduction of fibrinogen adsorption on PEG-coated polystyrene surfaces," J. Biomed. Mater. Res., vol. 26, pp. 779–790 (1992). Tethering of the active molecules decreases unproductive diffusion and increases the probability of successful interactions with target molecules or cells. Additionally, we have determined that if the linear tether is of sufficient length (about 30–150 nm), it kept the tethered-molecule away from the hydrogel surface and removed from any non-specific protein that may absorb to the hydrogel surface. From prior contact lens research, it is known that the adsorbed protein layer on hydrogel lenses is generally in the range of 0.6 to 1° g/cm$^2$ in a tri-layer configuration, corresponding to a thickness that is less than the effective length of the tether. Proteins passively adsorbed to the surface will therefore not interfere with the function of the tethered molecules in enhancing epithelial cell attachment to the tether-modified hydrogel surfaces. Although the linear tether is mobile, and can twist and bend, it is generally thermodynamically unfavorable for the tether to bend sufficiently to allow the tethered molecule to interact with adsorbed protein on the hydrogel surface. Unlike a branched or star formation tether, a linear chain allows the molecule attached to its free end to rotate and move in space. The linear tether allows the molecule to orient itself in the most favorable conformation for binding to the cell membrane.

By tethering laminin, fibronectin, substance P, insulin-like growth factor-1 (IGF-1) and ligand-specific chemical molecules such as the peptides that make up the carboxy-terminal heparin binding and cell adhesion-promoting domain of fibronectin [FAP], either singly or in various combinations, the natural cell adhesion and proliferation on a polymer surface is increased. The maintenance of the normal integrity of the corneal epithelium is regulated by both humoral and neural factors. Tether-modification involving various corneal enhancer molecules, such as laminin, fibronectin, substance P, FAP and IGF-1, was used to optimize the effects of these molecules on epithelial cell adhesion and spreading on synthetic biomaterial surfaces for uses in augmenting and/or replacing portions of the natural cornea. Additionally, a combination of laminin and fibronectin in approximately equal molar amounts was used. Adhesion of cells to a biomaterial surface is a major factor affecting biocompatibility. The addition of biological molecules to biomaterial surfaces should directly affect cell adhesion strength. The optimal tethered molecule-modified surfaces would have adhesion strengths more similar to those of natural stroma than those of protein-coated surfaces. This indicates that epithelial cells interact with the tethered molecule-modified surfaces as strongly as they interact with natural stroma.

Due to the specific radius of movement of the tether-molecule complex on the hydrogel surface, there is an optimal density of tethered proteins that will produce the maximal epithelial cell spreading and attachment response. By tailoring the number of binding sites on the polymer surface during the polymerization and by knowing the efficiency of binding, tethered-modified polymers may be optimized with differing densities of tethered-molecules on the surfaces.

Additionally, the surface topography of the synthetic corneal surface may play an important role in increasing and maintaining cell attachment in vivo. Although the exact function of Bowman's layer is not known, the micro and/or nanoscale texture imparted by this anterior layer of the stroma may be important in allowing the epithelial cells to withstand the shear force induced by blinking of the eyelids. The anterior surface of the synthetic material can be designed to mimic the surface topography of Bowman's layer. Several techniques may be used to produce the anterior surface such as micro-molding, etching, lathing or polymer engineering. To the resultant three-dimensional surface, corneal enhancer molecules of interest can be tethered. Such an engineered synthetic material which can support a normal corneal epithelium can be used for a corneal onlay, an epikeratophakia lenticule, an intracorneal augmentation device, or an artificial cornea.

EXAMPLE 1
Polymerization of a Base Optical Polymer (PHEMA/MAA).

While a wide range of optical polymers are potentially appropriate for our device, this example describes the use of a PHEMA/MAA hydrogel. Polymerization of the hydrogel was carried out using a photopolymerization system in a solvent solution that exchanges with water without changes in swelling, as originally described by M. J. Refojo, "Permeation of water through some hydrogels," J. Appl. Polym. Sci., vol. 9, pp. 3417–3426 (1965), and by U.S. Pat. No. 5,490,959. Specifically, for the PHEMA/5%MAA reaction, a blend of 95% (w/v) HEMA (hydroxyethyl methacrylate; Polysciences, Inc., Warrington, Pa.), 5% (w/v) MAA (methacrylic acid, Polysciences, Inc.), 0.78% EDGMA (ethylene glycol dimethacrylate; Polysciences, Inc.), 0.1% TMPTMA (trimethylolpropane trimethacrylate; Polysciences, Inc.), and 0.34% DAROCUR 1173 (Aldrich Chemical Co, Milwaukee, Wis.) was prepared. The monomer mix was added to 40% (w/v) GLUCAM E-20 (Amercol, New Jersey). The mixture was stirred under reduced pressure for 30 minutes at 25° C. and then transferred to sheet molds consisting of two silanized quartz plates separated by two 0.5 mm spacers. The filled molds were exposed to UV light (approximately 350 nm; 1.4 Joules/cm$^2$) for 20 minutes at 50° C. After polymerization, the gel solvent was exchanged with dimethylsulfoxide with no opaque transition phase. For the PHEMA/5% MAA/0.1% NDAM reaction, a blend of 94.9% (w/v) HEMA, 5% (w/v) MAA, 0.1% (w/v) NDAM, 0.78% EDGMA, 0.1% TMPTMA, and 0.34% DAROCUR 1173, was prepared and polymerized as outlined above.

Alternatively, a second base hydrogel, PHEMA/MAA/NDAM, which contains a small amount of positively charged monomer (N,N-dimethylaminoethylmethacrylate), can also be used for the surface. See P. Burgethon et al., "Modified hydroxyethylmethacrylate hydrogels as a modeling tool for the study of cell-substratum interactions," J. Cell Sci., vol. 92, pp. 111–121 (1989).

Tethering Reaction Sequences

To covalently tether the corneal enhancer molecules (e.g., laminin, fibronectin, substance P, IGF-1, and FAP) onto a PHEMA/(5%) MAA hydrogel surface, each of the corneal enhancer molecules were first covalently attached through an end terminus onto a polyethylene glycol (PEG, MW 3400) chain to form the PEGylated-molecule. Then the PEGylated-molecule was covalently attached to the exposed carboxyl groups on the surface of the PHEMA/5%MAA hydrogel by an esterification step to form the tether-modified surface. The density of carboxyl groups on the surface is determined by the percent MAA used in making the hydrogel. Because FAP, laminin and fibronectin have their cell active sites near the C-terminus, these molecules were tethered at their N-termini, whereas substance P and IGF-1 have N-terminus active sites, and therefore were tethered at their C-termini.

For FAP, laminin, fibronectin, which were tethered to the PEG chain through their N-termini using a succinimide-derivatized PEG, the general reaction sequence was the following:

Step One:

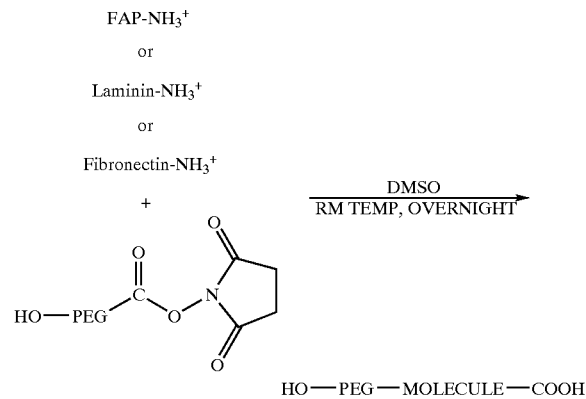

For substance P and IGF-1, which were tethered to the PEG chain through their C-termini, the general reaction sequence was the following:

Step One:

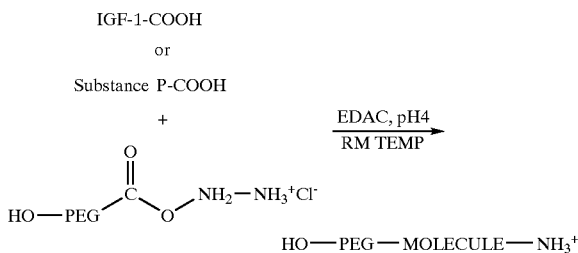

Each of the PEG reaction sequences was then molecular weight dialysis-purified against deionized water prior to attachment to the hydrogel. All tethered-molecules (ROH) were attached to the hydrogel surface by the following reaction:

Step Two:

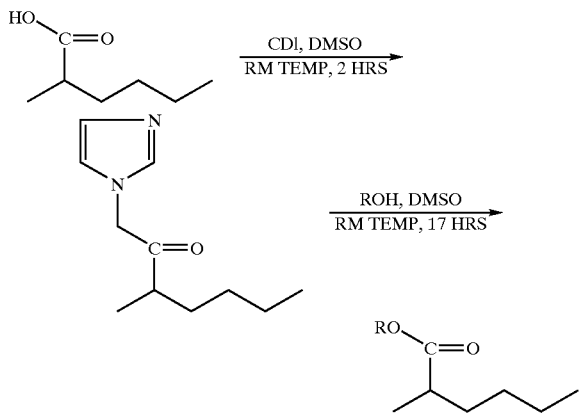

In the above reactions, the following abbreviations are used: DMSO=dimethyl sulfoxide; EDAC=ethyldimethyl (aminopropyl)carbodiimide; HOBT=hydroxybenzotriazole; CDI=carbonyldiimidazolle (Aldrich Chemical Co., Milwaukee, Wis.); and ROH=PEGylated-molecule.

The base hydrogel remained hydrated throughout the coupling procedure. For combination tether-modified surfaces, the stoichiometric amount of PEGylated-molecule used in the reaction sequence consisted of a ratio of laminin, fibronectin, substance P, IGF-1 and/or FAP. To date, three combinations of laminin and fibronectin have been made: 25:75, 50:50 and 75:25. The 50:50 combination has been tested, and it proved to be better (e.g. cells reached confluence across the surface faster) than either laminin, fibronectin, Substance P, or IGF-1 alone. However, FAP alone did as well as the 50:50 laminin:fibronectin combination. After coupling, the tether-modified hydrogels were sterilized by UVB light as described by L. Civerchia-Perez et al., "Use of collagen-hydroxyethylmethacrylate hydrogels for cell growth," Proc. Natl. Acad. Sci., vol. 77, pp. 2064–2068 (1980), and stored under sterile conditions until use.

Any non-specific adsorption of the molecule to be tethered to the hydrogel surface should be eliminated by first attaching the molecule to the tether (e.g. PEG chain), and then attaching the tether to the hydrogel surface, rather than attaching the PEG chain to the surface and then adding the molecule. Additionally, by tethering the molecule to the PEG chain prior to coupling the PEGylated-molecule to the hydrogel, the potential for coupling to occur within the hydrogel network should be significantly decreased due to the increased size and decreased diffusability of the tether-molecule complex.

Appropriate ratios of reactants for the various PEGylated-molecules may readily be determined by a person of ordinary skill in the art.

Analysis of PEGylated-Molecules

PEGylated-molecules were purified by dialysis, precipitated and dried at the end of the coupling reaction. Fourier-transformed infrared spectropscopy was performed to verify the coupling reaction. Peak heights and areas on each scan were identified and compared to starting materials. The scans were analyzed and compared to confirm the generation of peaks corresponding to the bonds that should have been formed during coupling. The activity of the PEGylated-molecule was analyzed using a monoclonal antibody test, ELISA (see methodology published in Current Protocols in Immunology, Chap. 2, "Enzyme-linked immunosorbent assays," NIH (eds.), Green Publishing Associates, Inc. and John Wiley & Sons, Inc., 2001). The results of the ELISA test using the PEGylated-molecule were compared to results of ELISAs with the plain molecule. The results for laminin, fibronectin, substance P, FAP and IGF-1, alone and for the laminin/fibronectin combination indicated that the tether did not prevent the antibody complex from forming with the PEGylated-molecules.

Analysis of Modified Polymer Surfaces

The tethered molecule-modified polymer surfaces were analyzed to determine the amount of tethered molecule coupled to the polymer surface. Radiolabeled molecules were used for this study. A radiolabeled PEGylated-molecule was chemically coupled to the hydrogel surface, the surface rinsed appropriately, and the material counted for radioactivity. A piece of hydrogel material that had radiolabeled PEGylated-molecule pipetted onto the surface and then rinsed served as the control. The results for laminin, fibronectin, alone and in combination confirmed an approximately 60% coupling efficiency or addition efficiency by the coupling reaction.

Additional analysis was also performed using X-ray Photoelectron Spectroscopy (XPS) to determine the chemical structure of the tethered molecules and the surface as a unit. The results of the XPS study showed an increase in nitrogen content proceeding away from the surface of the tethered molecule-modified polymer surface. Atomic force microscopy (AFM) studies were also performed to determine the spatial addition of the tethered molecule to the surface. The AFM tip was modified with antibody to tethered molecules to increase the efficiency of this analysis method. The results of the AFM analysis on laminin and fibronectin alone and in combination, indicate that the tethered molecules were distributed fairly evenly across the polymer surfaces.

Cellular Response to Modified Polymer Surfaces.

The cellular response to the tethered molecule-modified polymer surface was analyzed using in vitro primary rabbit corneal epithelial cell culture (see methods published in F. W. Stocker et al, "A tissue culture technique for growing corneal epithelial, stromal, and endothelial tissues separatel," Am. J. Ophthalmol. vol. 46(5, 11), pp. 294–298 (1958) and I. K. Gipson et al, "A technique for obtaining sheets of intact rabbit corneal epithelium, "Invest. Ophthalmol. Vis. Sci., vol. 23, pp. 269–273 (1982). Tether-modified surfaces, using laminin, fibronectin, substance P, FAP, and IGF-1 alone and a combination of laminin/fibronectin proved to be more like the natural substrate than were simple protein-coated surfaces. Among the tether-modified surfaces, FAP and the combination of laminin/fibronectin proved to be the best. Therefore, it is believed that epithelial cells will more readily spread and form focal adhesions on the tether-modified surfaces than on pure protein-coated surfaces. The cellular response was compared to plain polymer surfaces and polymer surfaces coated with the molecules. The results showed that all tethered molecule-modified polymer surfaces had significant cell growth by day 5 and were confluent by day 15. Plain polymer surfaces had little to no cell growth by day 15 of the cell culture, while molecule coated polymer surfaces had less than 40% confluence of cell growth by day 15.

Cellular identification and adherent morphology were also analyzed. AE5 antibody stain was used to prove that the cells on the surface were epithelial cells and not keratocytes that had invaded the cell culture by stromal contamination. Additionally, F-actin staining for actin filaments involved in focal adhesion complexes was performed. Normal adherent-cell morphology is characterized by pronounced cell spreading and by formation of actin stress fibers. It was therefore expected that adherent-cell morphology on the tether-modified hydrogel surfaces would be similar to or more normal than the morphology of the cells adherent to the protein-coated wells. The results showed that the epithelial cells responded to the tether-modified surfaces significantly better than they did to the protein-coated surfaces.

Strength of Cellular Adhesion

The strength of the cellular adhesion to the tethered molecule-modified surfaces was investigated using a jet impingement technique based on published methodology by K. Bundy et al, "Quantification of fibroblast adhesion to biomaterials using a fluid mechanics approach," J. Mater. Sci. Mater. Med., vol. 5, pp. 500–502 (1994) and R. G. Richards et al, "Microjet impingement followed by scanning electron microscopy as a qualitative technique to compare cellular adhesion to various biomaterials," Cell. Biol. Int., vol. 19, pp. 1015–1024 (1995). The results of these studies showed that cells grown on tethered molecule-modified polymer surfaces, using laminin, fibronectin, FAP, substance P, IGF-1 alone and a combination of laminin/fibronectin, were more strongly adherent to the underlying polymer than those cells grown on protein coated polymer surfaces.

EXAMPLE 2

Analysis of Corneal Cell Response to RGD-Modified Surfaces

The purpose of this study was to determine if a single peptide cell-adhesion sequence, RGD, amphoterically linked to the surface of a hydrogel, would enhance rabbit corneal epithelium adhesion and spreading. Two hydrogel surfaces, a hydrophilic polyurethane with surface-modifying end groups of poly(vinyl alcohol) (Polymer Technology Group, Berkeley, Calif.) and a poly(2-hydroxyethylmethacrylate/methacrylic acid) copolymer (PHEMA/MAA) (Vistakon, Jacksonville, Fla.) were used as the base materials. Amphoterically-modified RGD sequences (PepTite 2000) were obtained from Telios Pharmaceuticals, Inc. (San Diego, Calif.). PepTite-2000 uses a spacer arm consisting of amino acid sequences attached to the RGD sequence. The resulting peptide has the ability to coat a variety of materials non-covalently and present an accessible RGD sequence for cell attachment, as described in U.S. Pat. No. 5,120,829.

To test whether the RGD sequences on the modified surfaces were active, all four surface types (unmodified hydrogel, and hydrogel with RGD amphoterically attached for both types of hydrogel) were sterilized as described in L. Civerchia-Perez et al., "Use of collagen-hydroxyethylmethacrylate hydrogels for cell growth," Proc. Natl. Acad. Sci., vol. 77, pp. 2064–2068 (1980), and exposed to MG63 osteosarcoma cells as well as primary rabbit corneal keratocytes (stromal cells) and epithelial cell.

In this study, two types of cell cultures were used: 1) based on a corneal button outgrowth study (See D. K. Petit et al., "Influence of the substrate binding characteristics of fibronectin on corneal epithelial cell outgrowth," J. Biomater. Res., vol. 26, pp. 1259–1275 (1992); and 2) using regular cell culture techniques. The cultures were followed for 2 weeks to determine whether there was a difference in cell response to the materials tested. The results showed that the RGD sequence attached to the hydrogel surfaces functioned as a ligand for cell-adhesion receptors on both sarcoma and keratocyte cells, but was inactive for epithelial cell-adhesion receptors. The RGD sequence did not adequately mimic the cell-adhesion binding sites of the extracellular matrix proteins recognized by corneal epithelium. Without wishing to be bound by this theory, it is believed that tethering specific extracellular matrix proteins in their natural quaternary state, or tethering other ligand-specific chemical molecules such as FAP, or growth factors will significantly improve cell adhesion on hydrogels over that seen with only the RGD peptide.

EXAMPLE 3

Artificial Cornea with Tethered Molecule-Modified Polymer Optic Surface

Most artificial cornea devices or keratoprostheses are designed with a central optical area and a circumferential porous portion. The central optic is exposed to the pre-corneal area of the eye while the porous portion is embedded within the natural corneal remnants or sclera. Cellular in growth into the porous portion helps anchor the device in place. Polymer optic surfaces of artificial corneas implanted in rabbit corneas have been reported to take up to 3 weeks for epithelialization, if they epithelize at all. See J. T. Jacob-LaBarre et al., "Development of a new type of artificial cornea for treatment of endstage corneal diseases," in Progress in Biomedical Polymers (C G Gebelein and R L Dunn, eds.), Plenum Press, New York, pp. 27–39 (1990). Generally, the surfaces of such polymer surfaces differ primarily in their overall surface charge distribution. It is expected that the tethered corneal enhancer molecules will significantly reduce the time required for epithelialization over the optical surface of an artificial cornea device. FAP, laminin, and fibronectin interact at the cell membrane, while Substance P functions intracellularly. It is expected that tether-modified surfaces with only a membrane-active molecule present will induce epithelialization more rapidly than tether-modified surfaces with only an intracellularly active molecule. However, a surface bearing all of the tethered proteins should provide a better epithelialization rate, as it will more closely mimic the natural environment of the basement membrane.

EXAMPLE 4

Micro-Texture of the Anterior Surface of the Synthetic Corneal Surface

In addition to adding specific protein moieties to the surface to increase cell membrane/surface interactions and decrease indiscriminate protein adsorption, the anterior surface of the artificial cornea material may be microtextured, down to the nanoscale, to mimic the anterior surface of Bowman's layer found in the natural cornea. This micro and/or nanoscale texturing of the anterior surface of the synthetic corneal material can be performed prior to the addition of the specific protein moieties, either during polymerization, within the molding process, or as a post-polymerization process. Initially, the surface topography of the Bowman's layer can be carefully analyzed after carefully removing the epithelium while maintaining stromal hydration. This analysis is performed on dehydrated and frozen samples using both scanning electron microscopy (SEM) and atomic force microscopy (AFM). Using the data from these two analytical techniques, a 3-dimensional computer image of the anterior surface of Bowman's layer can be generated. This surface topographical image can then be reversed into the anterior surface of the mold within which the synthetic material would be molded. Additional methodologies to generate the 3-dimensional surface image on the synthetic material surface, such as etching, lathing or polymer engineering (using the porosity and polymer structure of the anterior surface of the synthetic material), may be used. Such micro/nano-textured synthetic material which can support a normal corneal epithelium can be used for a corneal onlay, an epikeratophakia lenticule, an intracorneal augmentation, or an artificial cornea.

The complete disclosures of all references cited in this specification are hereby incorporated by reference. Also incorporated by reference is the complete disclosure of the following: (1) Abstract and grant proposal submitted by Jean T. Jacob to the National Institute of Health and funded on Apr. 1, 1999 as Grant No. R01EV1236-01; and (2) J. R. Rochefort and J. T. Jacob, "Effect of surface active proteins and peptides on rabbit corneal epithelial cell growth," in Abstract for the 6$^{th}$ World Biomaterials Congress, May 15–20, 2000. In the event of an otherwise irreconcilable conflict, however, the present specification shall control.

We claim:

1. A device for corneal augmentation or replacement to improve vision which device is adapted to enhance and maintain a surface of corneal epithelial cells, said device comprising:

an optical polymer;

biocompatible, linear, single chain tethers;

corneal enhancer molecules to enhance corneal epithelial cell adhesion and migration;

wherein one end of each tether is linked to the surface of the optical polymer and the other end linked to a corneal enhancer molecule; and wherein the size of the tether is sufficient to allow the corneal enhancer molecule to maintain its active conformation state when linked to the polymer surface; and wherein the concentration of corneal enhancer molecules is such that the growth rate of corneal epithelial cells over the device is enhanced over the growth rate over an otherwise identical device lacking the tethers and corneal enhancer molecules.

2. The device of claim 1, wherein the optical polymer is a hydrogel.

3. The device of claim 1, wherein the optical polymer is comprises one or more compounds selected from the group consisting of collagen, polyurethanes, poly(2-hydroxyethylmethacrylate), polyvinylpyrolidone, polyglycerolmethacrylate, polyvinyl alcohol, polyethylene glycol, polymethacrylic acid, silicones, polyfluorocarbons, and polymers with phosphocholine.

4. The device of claim 1, wherein the molecular weight of the tethers is from about 2000 to about 8000.

5. The device of claim 1, wherein the molecular weight of the tethers is about 3400.

6. The device of claim 1, wherein the tethers comprise linear, single chain polymers.

7. The device of claim 1, wherein the tethers comprise poly(ethylene)glycol.

8. The device of claim 1, wherein the tethers comprise a linear, chain of amino acids or peptides.

9. The device of claim 1, wherein the corneal enhancer molecules comprise one or more compounds selected from the group consisting of extracellular matrix proteins, corneal growth factors, and other ligand-specific corneal enhancer sequences.

10. The device of claim 1, wherein the corneal enhancer molecules comprise one or more compounds selected from the group consisting of fibronectin, laminin, kalinin, K-laminin, vitronectin, talin, integrin, albumin, insulin-like growth factor, fibroblast growth factor, hepatocyte growth factor, epithelial growth factor, transforming growth factor-α, transforming growth factor-β, keratinocyte growth factor, heparin binding factor, fibroblast growth factor, nerve growth factor, substance P; interleukin-1 alpha, interleukin-1 beta, FAP, YIGSR, SIYITRF, PHSRN, IAFQRN, and LQVQLSIR.

11. The device of claim 1, wherein the corneal enhancer molecules comprise a combination of fibronectin and laminin.

12. The device of claim 11, wherein there are approximately equal molar amounts of fibronectin and laminin.

13. The device of claim 1, wherein the corneal enhancer molecules comprise FAP.

14. The device of claim 1, wherein said device comprises a three-dimensional synthetic surface that mimics the surface topography of the top layer of Bowman's membrane, such that the synthetic surface increases the surface interaction between the device and the corneal epithelial cells.

15. The device of claim 1, wherein the device is adapted for use as a corneal onlay, an epikeratophakia lenticule, an intracorneal augmentation, or an artificial cornea.

16. The device of claim 1, wherein the device is adapted for use as part of another device to augment or replace the natural cornea.

17. The device of claim 1, wherein the device has a refractive index similar to that of a natural cornea.

18. A device for corneal augmentation or replacement to improve vision which device is adapted to enhance and maintain a surface of corneal epithelial cells, said device comprising:

a PHEMA/MMA optical polymer;

poly(ethylene glycol) tethers with a molecular weight of 3400;

fibronectin and laminin molecules to enhance corneal epithelial cell adhesion and migration;

wherein one end of each tether is linked to the surface of the optical polymer and the other end linked to either a fibronectin or laminin molecule; and wherein the size of the tether is sufficient to allow the molecule to maintain its active conformation state when linked to the polymer surface; and wherein the concentration of molecules is such that the growth rate of corneal epithelial cells over the device is enhanced over the growth rate over an otherwise identical device lacking the tethers and molecules.

19. A method for corneal augmentation or replacement to improve vision, comprising implanting in the eye a device which is adapted to enhance and maintain a surface of corneal epithelial cells, said device comprising:

an optical polymer;

biocompatible, linear, single chain tethers;

corneal enhancer molecules to enhance corneal epithelial cell adhesion and migration;

wherein one end of each tether is linked to the surface of the optical polymer and the other end linked to a corneal enhancer molecule; and wherein the size of the tether is sufficient to allow the corneal enhancer molecule to maintain its active conformation state when linked to the polymer surface; and wherein the concentration of corneal enhancer molecules is such that the growth rate of corneal epithelial cells over the device is enhanced over the growth rate over an otherwise identical device lacking the tethers and corneal enhancer molecules.

20. The method of claim 19, wherein the optical polymer is a hydrogel.

21. The method of claim 19, wherein the optical polymer is comprises one or more compounds selected from the group consisting of collagen, polyurethanes, poly(2-hydroxyethylmethacrylate), polyvinylpyrolidone, polyglycerolmethacrylate, polyvinyl alcohol, polyethylene glycol, polymethacrylic acid, silicones, polyfluorocarbons, and polymers with phosphocholine.

22. The method of claim 19, wherein the molecular weight of the tethers is from about 2000 to about 8000.

23. The method of claim 19, wherein the molecular weight of the tethers is about 3400.

24. The method of claim 19, wherein the tethers comprise linear, single chain polymers.

25. The method of claim 19, wherein the tethers comprise poly(ethylene)glycol.

26. The method of claim 19, wherein the tethers comprise a linear, chain of amino acids or peptides.

27. The method of claim 19, wherein the corneal enhancer molecules comprise one or more compounds selected from the group consisting of extracellular matrix proteins, corneal growth factors, and other ligand-specific corneal enhancer sequences.

28. The method of claim 19, wherein the corneal enhancer molecules comprise one or more compounds selected from the group consisting of fibronectin, laminin, kalinin, K-laminin, vitronectin, talin, integrin, albumin, insulin-like growth factor, fibroblast growth factor, hepatocyte growth factor, epithelial growth factor, transforming growth factor-α, transforming growth factor-β, keratinocyte growth factor, heparin binding factor, fibroblast growth factor, nerve growth factor, substance P; interleukin-1 alpha, interleukin-1 beta, FAP, YIGSR, SIYITRF, PHSRN, IAFQRN, and LQVQLSIR.

29. The method of claim 19, wherein the corneal enhancer molecules comprise a combination of fibronectin and laminin.

30. The method of claim 28, wherein there are approximately equal molar amounts of fibronectin and laminin.

31. The method of claim 19, wherein said device comprises a three-dimensional synthetic surface that mimics the surface topography of the top layer of Bowman's membrane, such that the synthetic surface increases the surface interaction between the device and the corneal epithelial cells.

* * * * *